(12) United States Patent
Ikoma et al.

(10) Patent No.: US 7,390,385 B2
(45) Date of Patent: Jun. 24, 2008

(54) GAS SENSOR

(75) Inventors: Nobukazu Ikoma, Nagoya (JP); Takeya Miyashita, Kasugai (JP); Akihiro Muroguchi, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 586 days.

(21) Appl. No.: 10/807,985

(22) Filed: Mar. 24, 2004

(65) Prior Publication Data
US 2005/0016849 A1   Jan. 27, 2005

(30) Foreign Application Priority Data
Mar. 31, 2003   (JP) ............................. 2003-093051

(51) Int. Cl.
*G01N 27/26* (2006.01)
(52) U.S. Cl. ........................ 204/428; 204/424
(58) Field of Classification Search ......... 204/424–429; 205/783.5–785; 73/23.31–23.32; 422/51
See application file for complete search history.

(56) References Cited

U.S. PATENT DOCUMENTS

| | | | | |
|---|---|---|---|---|
| 4,040,930 | A * | 8/1977 | Dillon | 204/429 |
| 4,597,850 | A | 7/1986 | Takahasi et al. | 204/426 |
| 4,683,049 | A | 7/1987 | Nakajima et al. | 204/428 |
| 5,238,552 | A | 8/1993 | Kato et al. | 204/428 |
| 5,879,525 | A | 3/1999 | Kato | 204/424 |
| 6,071,476 | A * | 6/2000 | Young et al. | 422/51 |
| 6,214,186 | B1 * | 4/2001 | Watanabe et al. | 204/428 |
| 6,279,376 | B1 * | 8/2001 | Yamada et al. | 73/23.2 |
| 6,348,141 | B1 | 2/2002 | Kato et al. | 204/428 |
| 6,780,298 | B2 * | 8/2004 | Nakamura et al. | 204/428 |
| 6,948,353 | B2 * | 9/2005 | Toguchi et al. | 73/23.31 |
| 2002/0100687 | A1 | 8/2002 | Atsumi et al. | |
| 2003/0121782 | A1 * | 7/2003 | Atsumi et al. | 204/424 |

FOREIGN PATENT DOCUMENTS

| | | |
|---|---|---|
| EP | 0 678 740 A1 | 10/1995 |
| EP | 0 974 836 A2 | 1/2000 |
| EP | 1 046 906 A2 | 10/2000 |
| JP | 56-168154 | 12/1981 |
| JP | 63-78265 | 5/1988 |
| JP | 1-168864 | 11/1989 |
| JP | 8-247995 | 9/1996 |
| JP | 8-271476 | 10/1996 |
| JP | 2641346 | 5/1997 |
| JP | 09-222416 | 8/1997 |
| JP | 11-337513 | 12/1999 |
| JP | 2000-028571 | 1/2000 |
| JP | 2000-304719 | 11/2000 |
| JP | 2001-221769 | 8/2001 |

* cited by examiner

*Primary Examiner*—Alexa D. Neckel
*Assistant Examiner*—Matthew J Merkling
(74) *Attorney, Agent, or Firm*—Burr & Brown

(57) ABSTRACT

A protective cover of a gas sensor includes an inner protective cover which covers at least an end portion of a sensor element, an outer protective cover which covers the inner protective cover, and an intermediate protective cover which is installed between the inner protective cover and the outer protective cover. $A1/A2 \geq 1$ provided that A1 represents a total opening area of the inner gas inlet holes provided for the inner protective cover, and A2 represents a total opening area of the outer gas inlet holes provided for the outer protective cover.

6 Claims, 19 Drawing Sheets

FIG. 6

|  | COMPARATIVE EXAMPLE 1 | EXAMPLE 1 | EXAMPLE 2 | EXAMPLE 3 |
|---|---|---|---|---|
| STANDARD ATTACHMENT | 4/20 | 0/21 | 2/22 | 0/19 |
| INCLINED ATTACHMENT | 15/20 | 3/20 | 14/20 | 1/21 |

GAS SENSOR

This application claims the benefit of Japanese Application 2003-093051, filed Mar. 31, 2003, the entirety of which is incorporated herein by reference.

BACKGROUND OF THE INVENTION

1. Field of the Invention

The present invention relates to a gas sensor for measuring gas components such as NO, $NO_2$, $SO_2$, $CO_2$, and $H_2O$, contained in the atmospheric air or the exhaust gas discharged from vehicles or automobiles, for example. In particular, the present invention relates to a gas sensor which has a protective cover surrounding a sensor element.

2. Description of the Related Art

A variety of gas sensors have been suggested and practically used. For example, there are oxygen sensors based on the use of oxygen ion conductors, NOx sensors (see Japanese Laid-Open Patent Publication No. 8-271476), HC sensors (see Japanese Laid-Open Patent Publication No. 8-247995), hydrogen sensors based on the use of proton ion conductors, $H_2O$ sensors, oxygen sensors based on the use of oxide semiconductors such as $SnO_2$ and $TiO_2$.

Among the gas sensors as described above, the oxygen sensor based on the use of $ZrO_2$ and the oxygen sensor based on the use of $TiO_2$ are widely used for controlling the oxygen concentration in the exhaust gas discharged from an automobile and/or controlling A/F (air-fuel ratio), because such gas sensors operate stably even in the environment of the exhaust gas discharged from an automobile. The NOx sensor, which is based on the use of $ZrO_2$, is also at the stage of practical use to control NOx discharged from an automobile.

As an oxygen sensor attached to an exhaust tube of an internal combustion engine, a sensor having a protective cover provided around a sensor element to bring about a uniform flow of the exhaust gas, or a sensor having a protective cover for avoiding condensed water produced upon the start-up of the engine (droplets of water) is used. Sensors described in U.S. Pat. Nos. 4,597,850 and 4,683,049 are known as oxygen sensors to each of which a protective cover of a double structure is attached.

As for the conventional protective covers as described above, if a water protective cover is used, the response of the gas sensor may be delayed. Accordingly, it has been suggested that an inner protective cover of a double-structure protective cover, which is disposed close to a sensor element, has inner gas inlet holes facing the sensor element for improving the response performance (Japanese Patent No. 2641346).

However, in the conventional protective cover, the gas sensor is supposed to be positioned upstream with respect to the catalyst. If the sensor and the cover are installed downstream with respect to the catalyst, a problem was found in relation to water resistance (performance to avoid condensed water produced upon the start-up of the engine). Further, another problem was found in relation to water resistance depending on the angle of attachment to the exhaust tube of the internal combustion engine.

In order to obtain the quick response performance, it is conceived to provide a structure in which the inflow amount of the measurement gas is increased. However, in this structure, the droplets of the condensed water produced upon the start-up of the engine also tend to come into the sensor element. That is, it is difficult to balance preventing the sensor element from the droplets of water with improving the response performance.

Further, considerable temperature change or fluctuation may occur in the sensor element as the measurement gas flows into the protective cover, and cracks may appear in the substrate of the sensor element.

SUMMARY OF THE INVENTION

The present invention has been made taking the foregoing problems into consideration, and an object thereof is to provide a gas sensor which makes it possible to effectively protect a sensor element from the droplets of water and reduce the temperature change of a sensor element caused by the inflow of the measurement gas without deteriorating the response performance and which is excellent in temperature characteristics and water resistance.

According to the present invention, there is provided a gas sensor comprising a sensor element which measures a predetermined gas component of an introduced measurement gas, and a protective cover which surrounds the sensor element, the protective cover including an inner protective cover which covers at least an end portion of the sensor element, an outer protective cover which covers the inner protective cover, and an intermediate protective cover which is installed between the inner protective cover and the outer protective cover, wherein the inner protective cover has a bottom-equipped cylindrical shape with a plurality of inner gas inlet holes which are formed at positions of a side surface thereof facing the sensor element and with at least one inner gas discharge hole which is formed at a bottom portion; the outer protective cover has a bottom-equipped cylindrical shape with a plurality of outer gas inlet holes, the outer gas inlet holes formed in a side surface of the outer protective cover at portions where the outer gas inlet holes do not face the inner gas inlet holes; the intermediate protective cover has at least intermediate gas inlet holes which are formed at positions where the intermediate gas inlet holes do not face the inner gas inlet holes and the outer gas inlet holes; and $A1/A2 \geq 1$ provided that A1 represents a total opening area of the inner gas inlet holes, and A2 represents a total opening area of the outer gas inlet holes.

Accordingly, the triple structure is provided, in which the intermediate protective cover is provided between the double structure comprising the inner protective cover and the outer protective cover. Therefore, it is possible to effectively avoid the droplets of water produced upon the start-up of the engine.

Further, the ratio A1/A2 between the total opening area A1 of the plurality of inner gas inlet holes and the total opening area A2 of the plurality of outer gas inlet holes is not less than 1. Therefore, the flow rate, at which the measurement gas flows from the outer gas inlet holes passes through the inner gas inlet holes, is reduced. Therefore, for example, even if the droplets of the condensed water enters the interior of the outer protective cover through the outer gas inlet holes, the droplets of the condensed water does not come to the sensor element through the inner gas inlet holes, because of the low flow rate of the measurement gas to flow into the inner gas inlet holes. As a result, for example, even when the protective cover is installed at any angle with respect to a gas tube (for example, an exhaust tube of an internal combustion engine), it is possible to avoid the droplets of water which would otherwise reach the sensor element. Of course, the measurement gas does not blow toward the sensor element fast. Therefore, it is possible to suppress the temperature change or fluctuation of the sensor element (temperature change or fluctuation caused by the introduction of the measurement gas).

Therefore, the protective cover may be attached approximately perpendicularly to the gas tube. Alternatively, the protective cover may be attached while being inclined to the gas tube. It is possible to realize a variety of forms of attachment to the gas tube in conformity with the preference of the user.

The response performance of the sensor element may be deteriorated due to the low flow rate of the measurement gas to the inner gas inlet holes. However, the deterioration of the response performance can be suppressed by appropriately selecting the diameters of the outer gas inlet holes and the inner gas inlet holes.

In the gas sensor structured as described above, it is also preferable that the number of the inner gas inlet holes may be larger than the number of the outer gas inlet holes. This arrangement decreases the flow rate of the measurement gas in the outer protective cover flowing into the inner gas inlet holes. Therefore, the measurement gas is diffused in the inner protective cover until arrival at the sensor element. It is possible to avoid any local and concentrated emission of the measurement gas to the sensor element.

Therefore, it is possible to avoid local temperature change in the sensor element, and it is possible to effectively avoid, for example, cracks which would be otherwise caused by the temperature change of the sensor element.

In the gas sensor described above, it is also preferable that the inner protective cover has plate sections each of which extends over each of inner gas inlet holes. Accordingly, the measurement gas coming into the inner protective cover through the inner gas inlet holes is diffused by the plate sections. That is, the sensor element is prevented from any direct blow of the measurement gas. It is possible to suppress the temperature change in the sensor element.

In the gas sensor constructed as described above, it is also preferable that the plurality of inner gas inlet holes are formed at approximately equal pitches along one circumference of the inner protective cover. Alternatively, when the plurality of inner gas inlet holes are classified into n groups, then the inner gas inlet holes in a first group are formed at approximately equal pitches along a first circumference of the inner protective cover, the inner gas inlet holes in a second group are formed at approximately equal pitches along a second circumference of the inner protective cover, . . . and similarly the inner gas inlet holes in an nth group are formed at approximately equal pitches along an nth circumference of the inner protective cover.

Usually, if the inner gas inlet holes are randomly formed, the measurement gas flows intensively toward the sensor element through one or two of the inner gas inlet holes depending on the arrangement state thereof.

However, when the plurality of inner gas inlet holes are formed along one circumference or a plurality of circumferences of the inner protective cover as described above, the measurement gas comes to the sensor element while being dispersed approximately uniformly with respect to the inner gas inlet holes. Therefore, it is possible to further reduce the flow rate of the measurement gas at each of the inner gas inlet holes, and it is possible to effectively protect the sensor element from the droplets of water. It is also possible to avoid intensive blow of the measurement gas against the sensor element. Therefore, it is possible to further suppress the temperature change in the sensor element.

The above and other objects, features, and advantages of the present invention will become more apparent from the following description when taken in conjunction with the accompanying drawings in which a preferred embodiment of the present invention is shown by way of illustrative example.

BRIEF DESCRIPTION OF THE DRAWINGS

FIG. 6 shows a table illustrating results of measurement as to whether sweat is on the sensor element;

DESCRIPTION OF THE PREFERRED EMBODIMENTS

Illustrative embodiments of the gas sensor according to the present invention will be explained below with reference to FIGS. 1 to 19.

Figure 1:
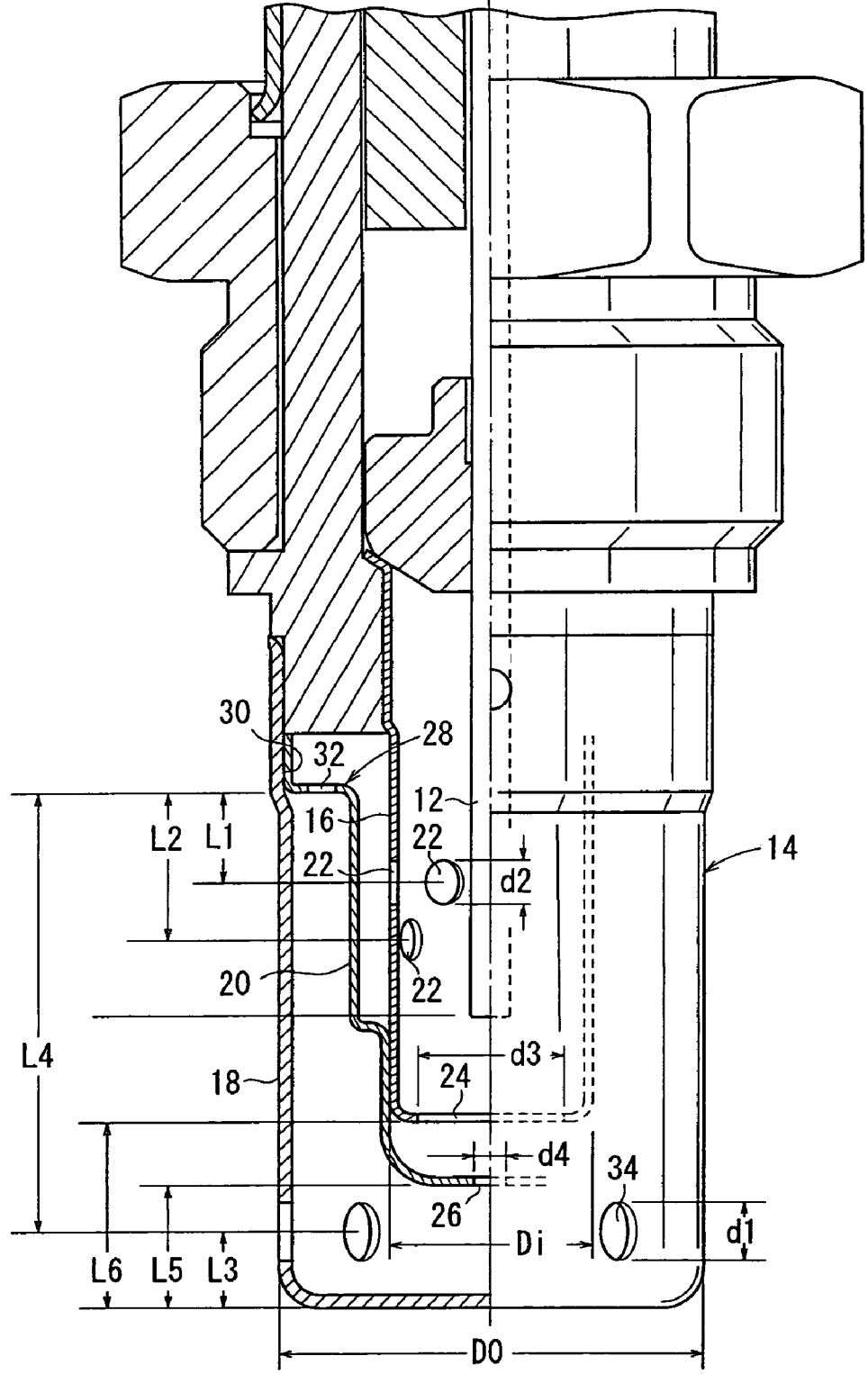
FIG. 1 is a sectional view illustrating, with partial omission, a gas sensor according to a first embodiment.

As shown in FIG. 1, a gas sensor 10A according to a first embodiment comprises a sensor element 12 which measures a predetermined gas component, for example, NOx contained in a measurement gas (exhaust gas), and a protective cover 14 which is arranged to surround an end portion of the sensor element 12.

Figure 3:
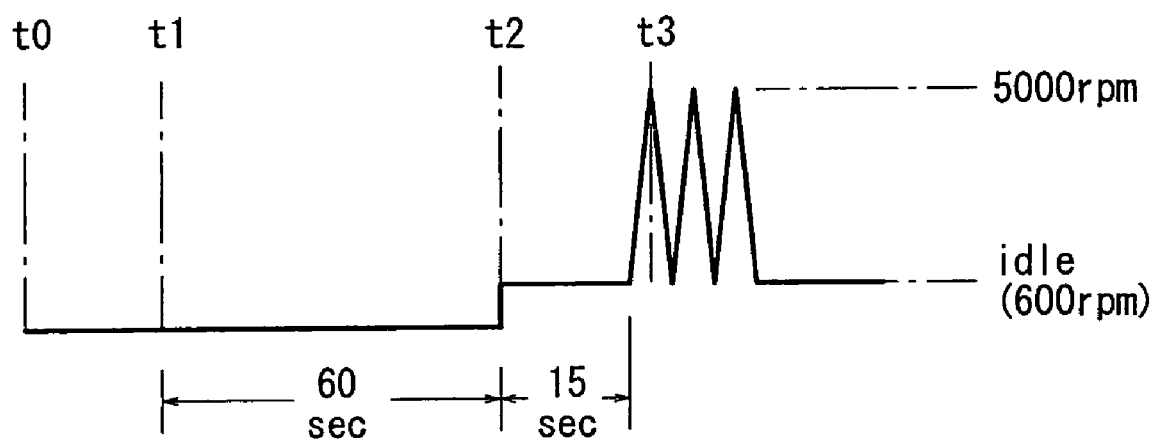
FIG. 3 shows a measuring timing used in relation to the first exemplary experiment.
Figure 4:
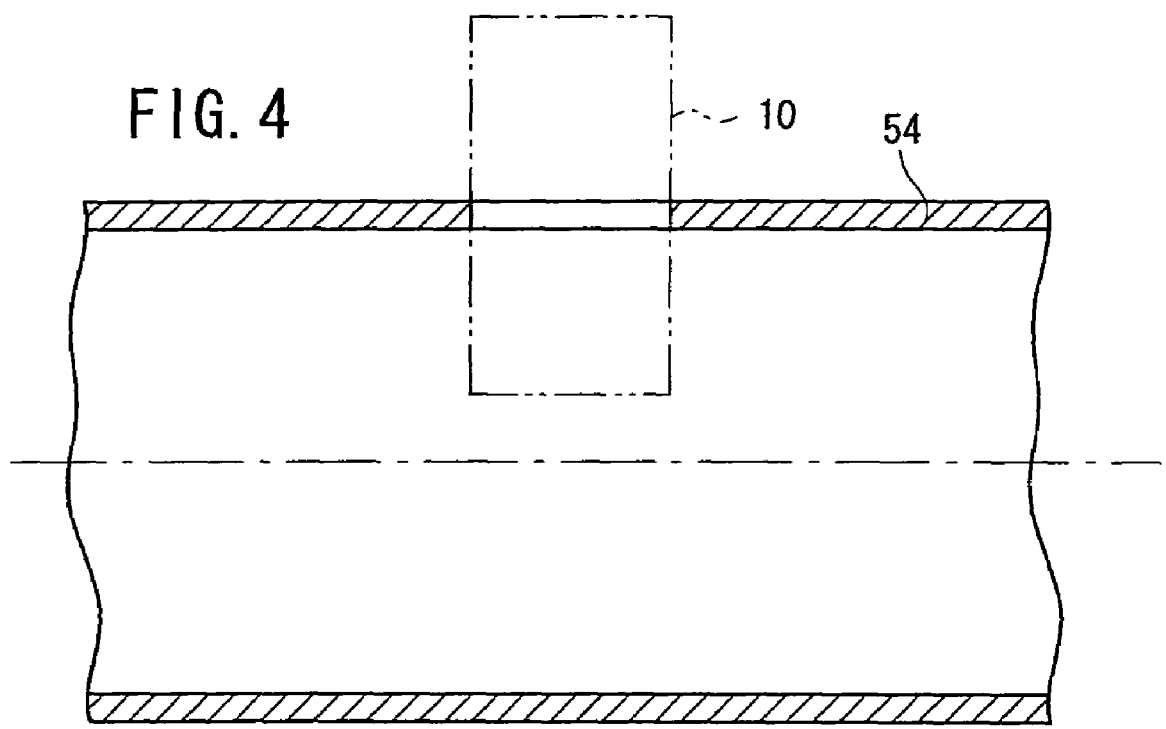
FIG. 4 illustrates standard attachment of the gas sensor.

The sensor element 12 is constructed in the same manner as a sensor element described, for example, in Japanese Laid-Open Patent Publication No. 2000-304719 (see FIGS. 3 and 4 of this patent document). Therefore, the explanation thereof will be herein omitted.

In the gas sensor 10A according to the first embodiment, the protective cover 14 surrounding the sensor element 12 comprises an inner protective cover 16 which covers the end portion of the sensor element 12, an outer protective cover 18 which covers the inner protective cover 16, and an intermediate protective cover 20 which is installed between the inner protective cover 16 and the outer protective cover 18.

The inner protective cover 16 is formed of metal and has a bottom-equipped cylindrical shape. The inner protective cover 16 has a plurality of inner gas inlet holes 22 which are formed at positions facing the sensor element 12. The inner protective cover 16 also has an inner gas discharge hole 24 which is formed at the bottom (an end portion).

The intermediate protective cover 20 is made of metal and has a bottom-equipped cylindrical shape. The end portion of the inner protective cover 16 is covered with the end portion of the intermediate protective cover 20. An intermediate gas discharge hole 26 is formed at the center of the end portion of the intermediate protective cover 20 and has a diameter smaller than the diameter of the inner gas discharge hole 24 of the inner protective cover 16.

The intermediate protective cover 20 has a flange section 28 at a rear portion that abuts against the inner wall of the outer protective cover 18. The flange section 28 is integrally formed with a bent section 30. The bent section 30 has a rear end portion which is bent laterally and has a circumferential end which is bent backwardly. The outer circumferential surface of the bent section 30 abuts against the inner wall of the outer protective cover 18.

The flange section 28 has a plurality of slits 32 which are formed along the circumference to define intermediate gas inlet holes. In the first embodiment, the six slits 32 are formed and equally arranged. Each of the slits 32 has a circular arc-shaped form with a central angle of 40° on the circumference of the flange section 28. There are circular arc-shaped intervals between the adjoining slits 32, and each of the intervals has a central angle of 20°.

The outer protective cover 18 is formed of metal and has a bottom-equipped cylindrical shape. The outer protective cover 18 has outer gas inlet holes 34. The outer gas inlet holes 34 are arranged in a side circumferential surface at portions where the outer gas inlet holes 34 do not face the inner gas inlet holes 22 of the inner protective cover 16.

The six outer gas inlet holes 34 are formed and arranged equally in the side circumferential surface of the outer protective cover 18 between the inner gas discharge hole 24 and the bottom of the outer protective cover 18.

The twelve inner gas inlet holes 22 are formed through a side circumferential surface of the inner protective cover 16 such that the holes 22 are provided in two vertically separated positions.

The positions at which the twelve inner gas inlet holes 22 are formed are explained below. Six inner gas inlet holes 22 are formed along one circumference disposed at a distance L1 from the flange section 28. Further, the other six inner gas inlet holes 22 are formed along one circumference disposed at a distance L2 (>L1) from the flange section 28. In order to maintain the rigidity of the inner protective cover 16, the positions where the respective inner gas inlet holes 22 are formed are set so that line segments connecting the centers of the respective inner gas inlet holes 22 make a polygonal curve, so called a zigzag line.

That is, the positional relationship of the outer gas inlet holes 34, the slits (intermediate gas inlet holes) 32, and the inner gas inlet holes 22 is established such that the outer gas inlet holes 34, the inner gas inlet holes 22, and the intermediate gas inlet holes 32 are arranged in this order from the bottom to an upper part of the outer protective cover 18.

The measurement gas coming through the outer gas inlet holes 34 of the outer protective cover 18 arrives at the sensor element 12 via the slits 32 of the intermediate protective cover 20 and the inner gas inlet holes 22 of the inner protective cover 16. After that, the measurement gas is discharged through the inner gas discharge hole 24 formed at the bottom of the inner protective cover 16, then through the intermediate gas discharge hole 26 formed at the bottom of the intermediate protective cover 20, and finally through the outer gas inlet holes 34 of the outer protective cover 18. It is assumed that this route is defined as the flow path for the measurement gas. Because the negative pressure is created in the vicinity of the intermediate gas discharge hole 26, the measurement gas smoothly flows through the flow path.

In the gas sensor 10A according to the first embodiment, $$A1/A2 \geq 1$$

provided that A1 represents the total opening area of the twelve inner gas inlet holes 22, and A2 represents the total opening area of the six outer gas inlet holes 34.

Accordingly, the intermediate protective cover 20 is provided between the double structure comprising the inner protective cover 16 and the outer protective cover 18, thereby providing a triple structure. Therefore, it is possible to effectively avoid the droplets of condensed water produced upon the start-up of the engine.

Further, the ratio A1/A2 between the opening areas A1 and A2 is not less than 1. Therefore, the flow rate at which the measurement gas comes from the outer gas inlet holes 34 passes through the inner gas inlet holes 22 is reduced.

Therefore, for example, even if the droplets of the condensed water enters the outer protective cover 18 through the outer gas inlet holes 34, the droplets of the condensed water does not come to the sensor element 12 through the inner gas inlet holes 22, because of the low flow rate of the measurement gas passing through the inner gas inlet holes 22.

As a result, for example, even if the protective cover 14 may be installed at any angle with respect to a gas tube (for example, an exhaust tube of an internal combustion engine), it is possible to prevent the sensor element 12 from the droplets of water. Of course, the measurement gas does not collide with the sensor element quickly. Therefore, it is possible to suppress the temperature change of the sensor element 12, such as changes caused by the inflow of the measurement gas.

Therefore, the protective cover 14 may be attached approximately perpendicularly with respect to the gas tube. Alternatively, the protective cover 14 may be attached while being inclined with respect to the gas tube. It is possible to realize various options in attachment to the gas tube in conformity with the preference of a user.

On the other hand, the response performance of the sensor element 12 may be deteriorated due to the low flow rate of the measurement gas into the inner gas inlet holes 22. However, the deterioration of the response performance can be minimized by appropriately selecting the respective diameters of the outer gas inlet holes 34 and the respective diameters of the inner gas inlet holes 22.

Further, in the first embodiment, the number of the inner gas inlet holes 22 is larger than the number of the outer gas inlet holes 34. Thus, the flow rate of the measurement gas into the outer protective cover 18 is decreased at the respective inner gas inlet holes 22. Therefore, the measurement gas is diffused in the inner protective cover 16 until arrival at the sensor element 12. It is possible to avoid any local and concentrated emission of the measurement gas to the sensor element 12.

As a result, it is possible to avoid the local temperature change in the sensor element 12, and it is possible to effectively avoid, for example, the appearance of a crack which would be otherwise caused by the temperature change of the sensor element 12.

Specific dimensions of the protective cover 14 may be described as follows by way of example. As for the outer protective cover 18, the outer diameter Do of the outer protective cover 18 is about 14.6 mm, the diameter d1 of the outer gas inlet holes 34 is about 2 mm, and the thickness of the outer protective cover 18 is about 0.4 mm.

As for the inner protective cover 16, the outer diameter Di is about 7 mm, the diameter d2 of the inner gas inlet holes 22 is about 1.5 mm, the diameter d3 of the inner gas discharge hole 24 is about 5.0 mm, and the thickness of the inner protective cover 16 is about 0.3 mm.

The diameter d4 of the intermediate gas discharge hole 26 provided at the bottom of the intermediate protective cover 20 is about 1 mm.

The distance L1 from the flange section 28 to the centers of the inner gas inlet holes 22 of a first group is about 3.5 mm. The distance L2 from the flange section 28 to the centers of the inner gas inlet holes 22 of a second group is about 5.5 mm. The distance L3 from the end of the outer protective cover 18 to the centers of the outer gas inlet holes 34 is about 2.8 mm. The distance L4 from the centers of the outer gas inlet holes 34 to the flange section 28 is about 16 mm. The distance L5 from the end of the outer protective cover 18 to the end of the intermediate protective cover 20 is about 4.5 mm. The distance L6 from the end of the outer protective cover 18 to the end of the inner protective cover 16 is about 6.5 mm.

Three exemplary experiments (first to third exemplary experiments) will now be described. In the first exemplary experiment, the sweat and the temperature change of the sensor element 12 are observed in relation to Comparative Example 1 and Examples 1 to 3.

Figure 2:
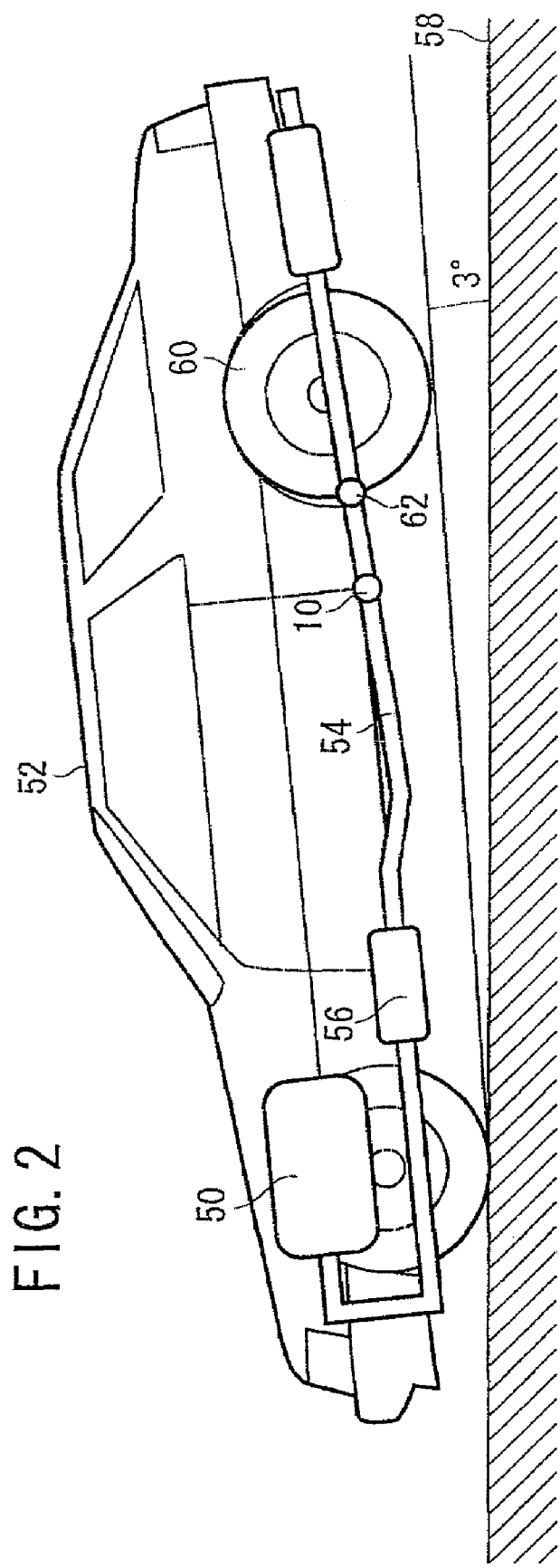
FIG. 2 illustrates a measuring method carried out in a first exemplary experiment.

As shown in FIG. 2, the gas sensor (indicated by reference numeral 10) was attached to a downstream portion with respect to a catalyst 56, of an exhaust tube 54 of an automobile 52 which carried a 2.0-liter gasoline engine 50. Further, the rear portion of the automobile 52 was lifted to incline the automobile 52 by 3° with respect to the ground 58.

As shown in FIG. 3, the water of 100 cc, which was colored with Japanese black ink or the like, was poured into a portion 62 of the exhaust tube 54 of the automobile 52 approximately corresponding to a back wheel 60 at a time point t0. The application of electric power to a heater of the gas sensor 10 was started at a time point t1 after several seconds to 10 seconds. The engine 50 was started (number of revolutions in the idle state=600 rpm) at a time point t2 after 60 seconds. The acceleration operation of 3 seconds (number of revolutions at the peak of the acceleration state=5,000 rpm) was performed continuously three times at a time point t3 after 15 seconds.

The judgment whether the droplets of water were on the sensor element 12 was made visually.

The temperature change of the sensor element 12 was measured as follows. In order to maintain a constant temperature of the sensor element 12, the amount of electric power application (electric power) to the heater was subjected to the feedback control depending on the change of the environmental temperature. Therefore, the difference was measured between the amount of electric power application (electric power) to the heater without wind and the amount of electric power application (electric power) to the heater brought about when the fluid flowed through the exhaust tube 54 at a flow rate of 45 m/sec, and the difference was used as a result of the measurement of the temperature change.

Figure 5:
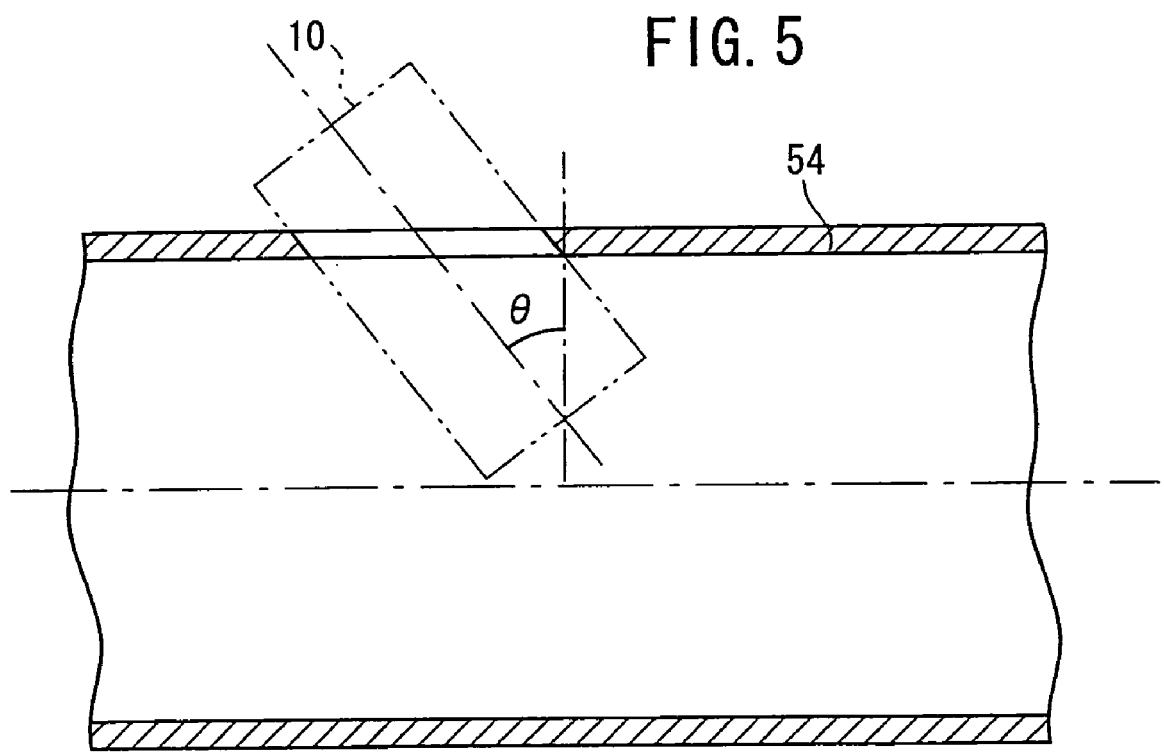
FIG. 5 illustrates inclined attachment of the gas sensor.

The measurement was performed when the gas sensor 10 was attached perpendicularly to the exhaust tube 54 (hereinafter referred to as "standard attachment") as shown in FIG. 4 and when the gas sensor 10 was attached while being inclined (angle of inclination θ=35°) to the exhaust tube 54 (hereinafter referred to as "inclined attachment") as shown in FIG. 5.

Comparative Example 1 was prepared such that the ratio A1/A2 between the total opening area A1 of the inner gas inlet holes 22 and the total opening area A2 of the outer gas inlet holes 34 was less than 1.

Example 1 was constructed such that the ratio A1/A2 was not less than 1, and the diameter of the outer gas inlet holes 34 was smaller than that of Comparative Example 1. Example 2 was prepared such that the ratio A1/A2 was not less than 1, and the number of the inner gas inlet holes 22 was larger than that of Comparative Example 1. Example 3 was prepared in the same manner as the gas sensor 10A according to the first embodiment described above, in which the ratio A1/A2 was not less than 1, the diameter of the outer gas inlet holes 34 was smaller than that of Comparative Example 1, and the number of the inner gas inlet holes 22 was larger than that of Comparative Example 1.

Figure 7:
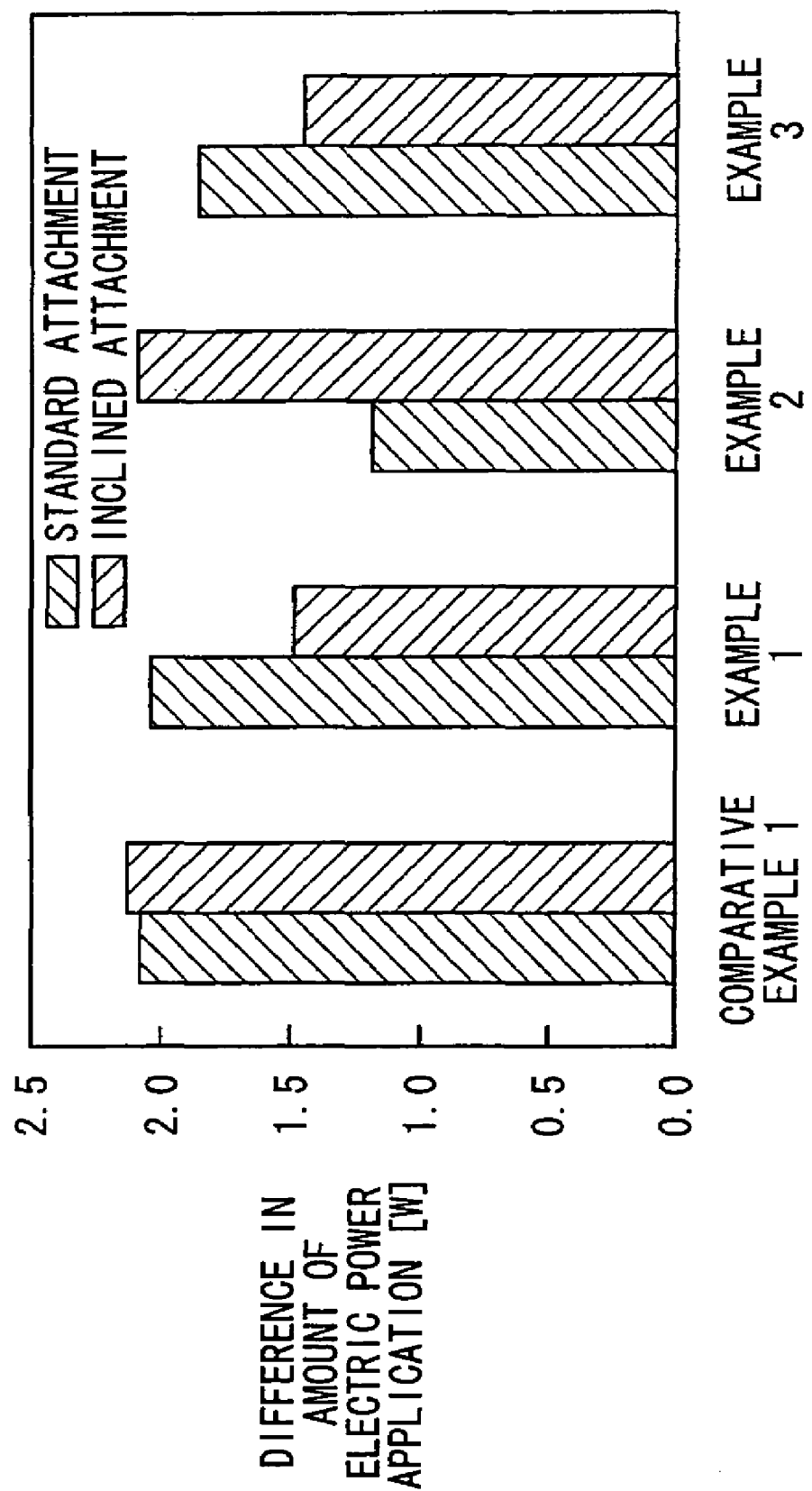
FIG. 7 shows a graph illustrating results of measurement of the temperature change of a sensor element.

FIG. 6 shows results of the measurement of wetting, and FIG. 7 shows results of the measurement of the temperature change of the sensor element 12. In FIG. 7, left bars indicate the cases of the standard attachment, and right bars indicate the cases of the inclined attachment.

FIG. 6 shows the result of measurement of wetting. In the case of the standard attachment, four out of twenty samples were NG (i.e., no good) in Comparative Example 1, two out of twenty-two samples were NG in Example 2, but no NG sample was found in both of Example 1 and Example 3.

In the case of the inclined attachment, fifteen out of twenty samples were NG in Comparative Example 1, three out of twenty samples were NG in Example 1, fourteen out of twenty samples were NG in Example 2, and one out of twenty-one samples was NG in Example 3.

As described above, in Comparative Example 1 and Example 2, the frequency of the occurrence of NG differed depending on the attachment state of the gas sensor 10. In particular, the occurrence of NG was conspicuous in the case of the inclined attachment. However, the number of NG samples was smaller in Example 2 than in Comparative Example 1.

On the other hand, the wetting was scarcely caused in Examples 1 and 3 irrelevant to the attachment state.

The temperature change of the sensor element 12 was observed as follows as shown in FIG. 7. In the case of the standard attachment, the differences in amount of electric power application were about 2.1 W in Comparative Example 1, about 2.05 W in Example 1, about 1.2 W in Example 2, and about 1.8 W in Example 3.

In the case of the inclined attachment, the differences in amount of electric power application were about 2.15 W in Comparative Example 1, about 1.5 W in Example 1, about 2.1 W in Example 2, and about 1.4 W in Example 3.

As described above, it is understood that, in Comparative Example 1, the difference in amount of electric power application is large and the temperature change is large irrelevant to the attachment state.

On the other hand, in Example 1, the temperature change is large in the standard attachment state in approximately the same manner as in Comparative Example, 1, but the difference in amount of electric power application is small in the inclined attachment state. In Example 2, the temperature change is large in the inclined attachment state in approximately the same manner as in Comparative Example 1, but the difference in amount of electric power application is small and the temperature change is small in the standard attachment state.

In Example 3, it is appreciated that the difference in amount of electric power application is small as compared with Comparative Example 1 in both of the standard attachment state and the inclined attachment state, and the temperature change of the sensor element 12 is suppressed regardless of the attachment state.

Next, in the second exemplary experiment, an observation was made for the response performance when the A/F (air-fuel ratio) was changed for Comparative Example 1 and Examples 1 to 3 described above.

Figure 8:
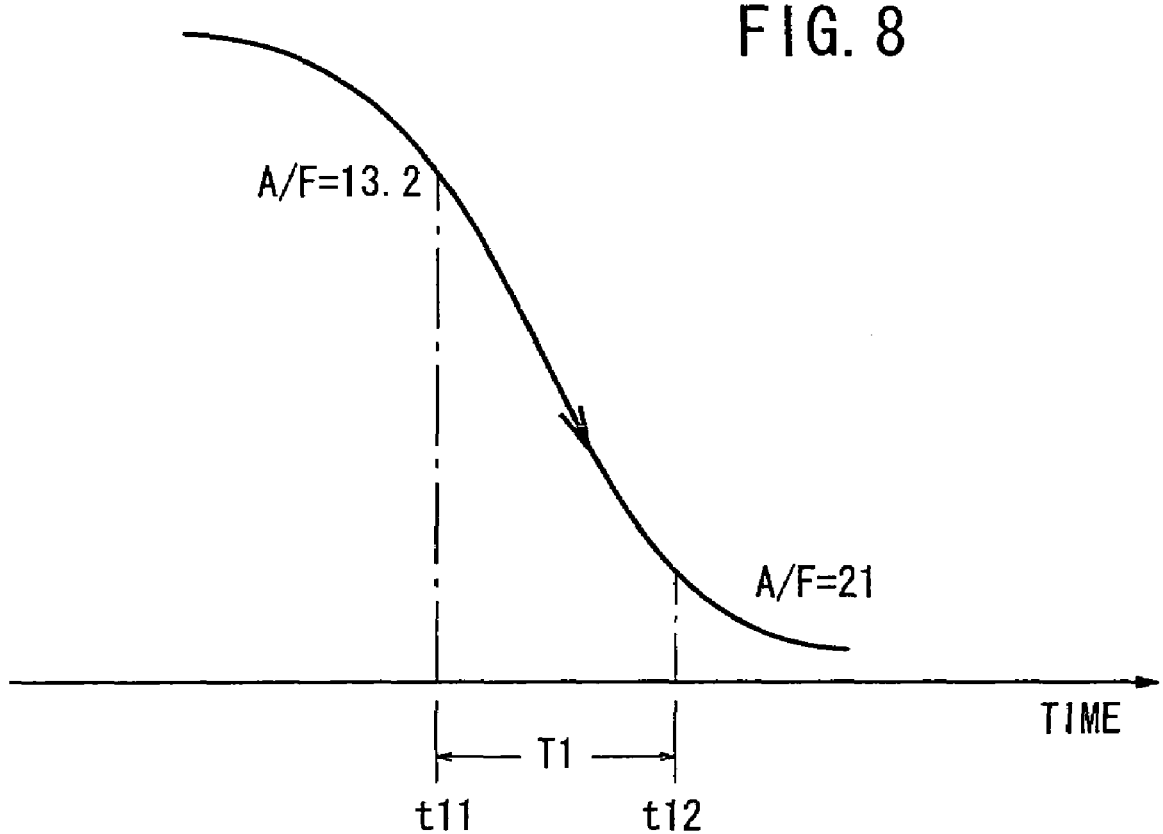
FIG. 8 illustrates the response time brought about when the fuel of an engine is changed from rich to lean.
Figure 9:
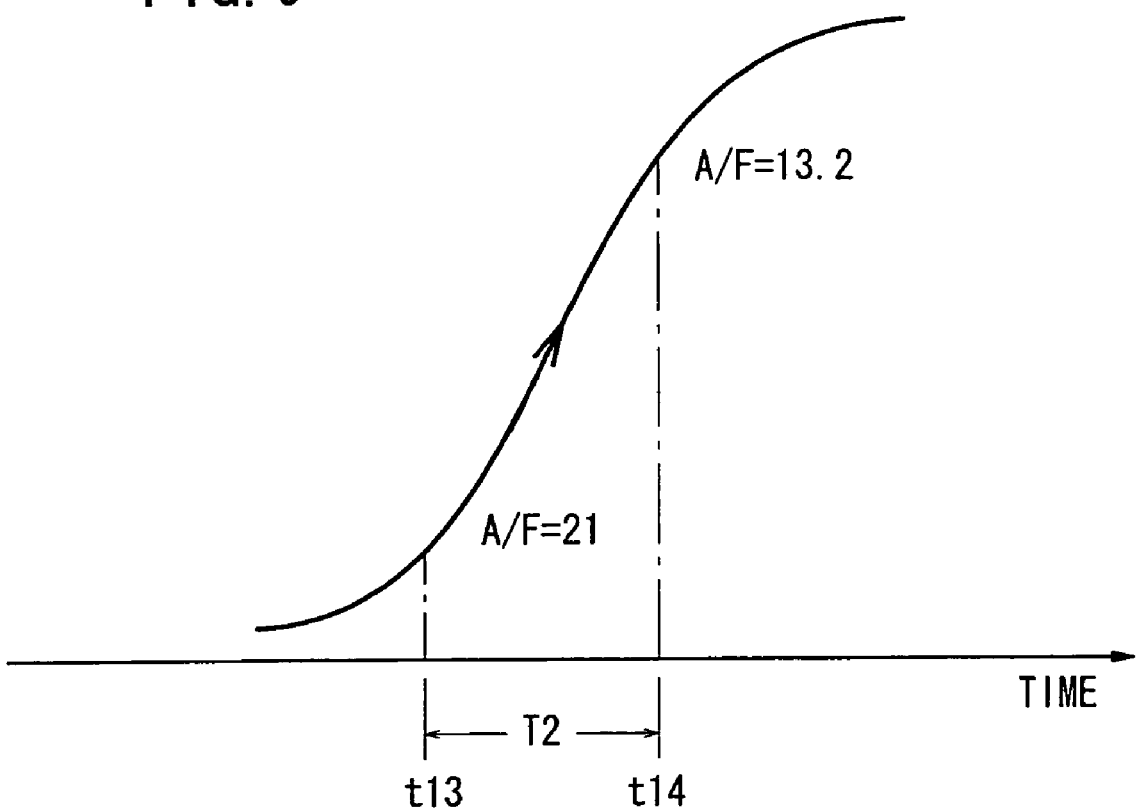
FIG. 9 illustrates the response time brought about when the fuel of the engine is changed from lean to rich.

An unillustrated 1.8-liter gasoline engine was used. Under a condition of 2,500 rpm/26 Nm and a gas temperature=380°, the gas sensor 10 was attached perpendicularly to the exhaust tube 54 as shown in FIG. 4. As shown in FIG. 8, a response time T1 was measured. The response time T1 ranged from a time point t11 at which the gas sensor 10 detected A/F=13.2 to a time point t12 at which the gas sensor 10 detected A/F=21 when the fuel was changed from rich to lean. Further, as shown in FIG. 9, a response time T2 was measured. The response time T2 ranged from a time point t13 at which the gas sensor 10 detected A/F=21 to a time point t14 at Which the gas sensor 10 detected A/F=13.2 when the fuel was changed from lean to rich.

Figure 10:
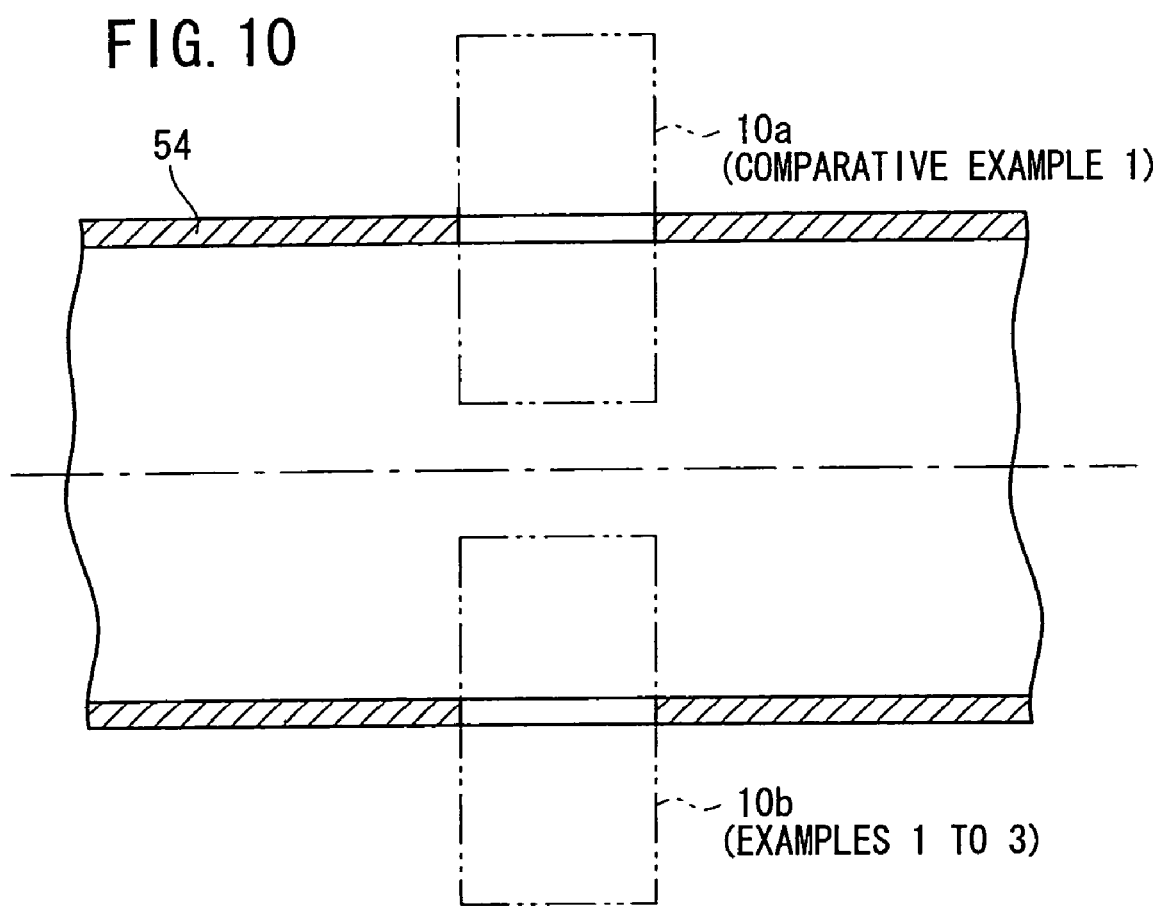
FIG. 10 illustrates attachment states of gas sensors for measuring the delay time.
Figure 11:
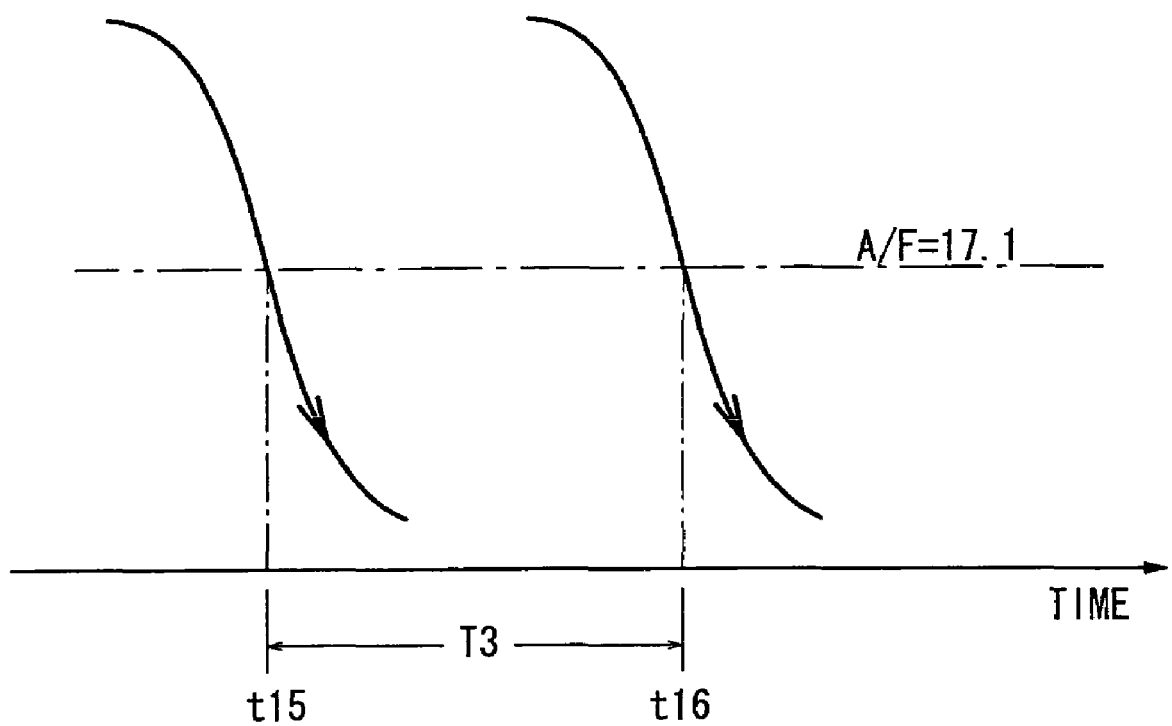
FIG. 11 illustrates the delay time brought about when the fuel of the engine is changed from rich to lean.
Figure 12:
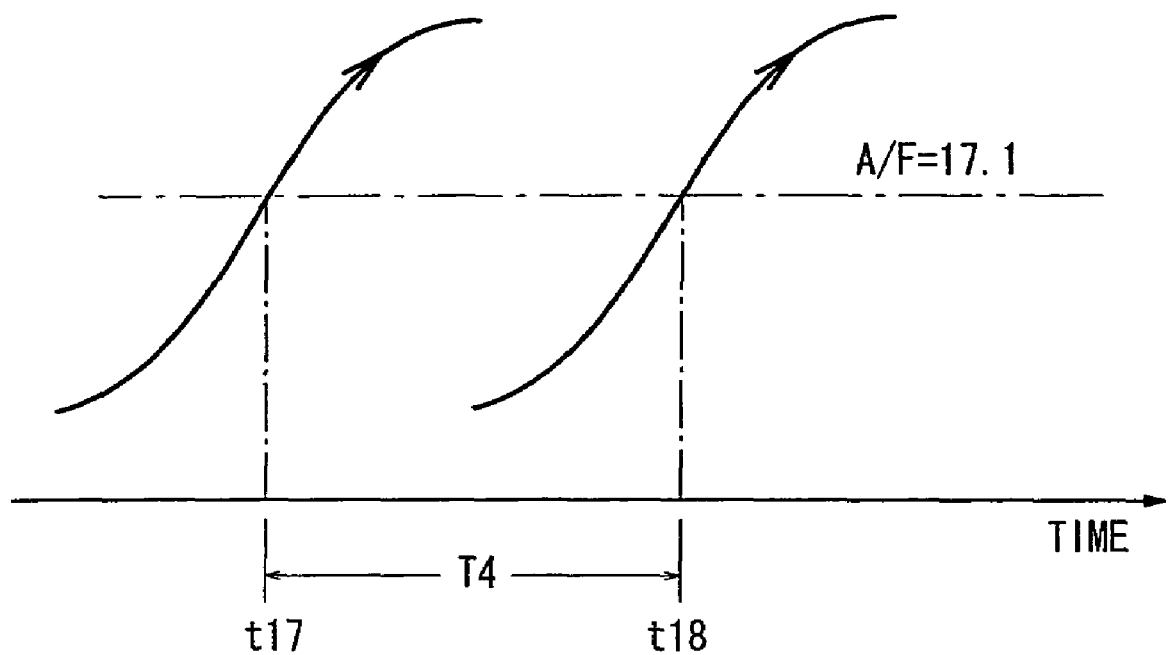
FIG. 12 illustrates the delay time brought about when the fuel of the engine is changed from lean to rich.

Further, as shown in FIG. 10, two gas sensors 10a, 10b were attached perpendicularly to the exhaust tube 54 so that the gas sensors 10a, 10b were opposed to one another. As shown in FIG. 11, a delay time T3 was measured. The delay time T3 ranged from a time point t15 at which one gas sensor 10a (Comparative Example 1) detected A/F=17.1 to a time point t16 at which the other gas sensor 10b (Example 1, 2, or 3) detected A/F=17.1 when the fuel was changed from rich to lean. Further, as shown in FIG. 12, a delay time T4 was measured. The delay time T4 ranged from a time point t17 at which one gas sensor 10a (Comparative Example 1) detected A/F=17.1 to a time point t18 at which the other gas sensor 10b (Example 1, 2, or 3) detected A/F=17.1 when the fuel was changed from lean to rich.

Figure 13:
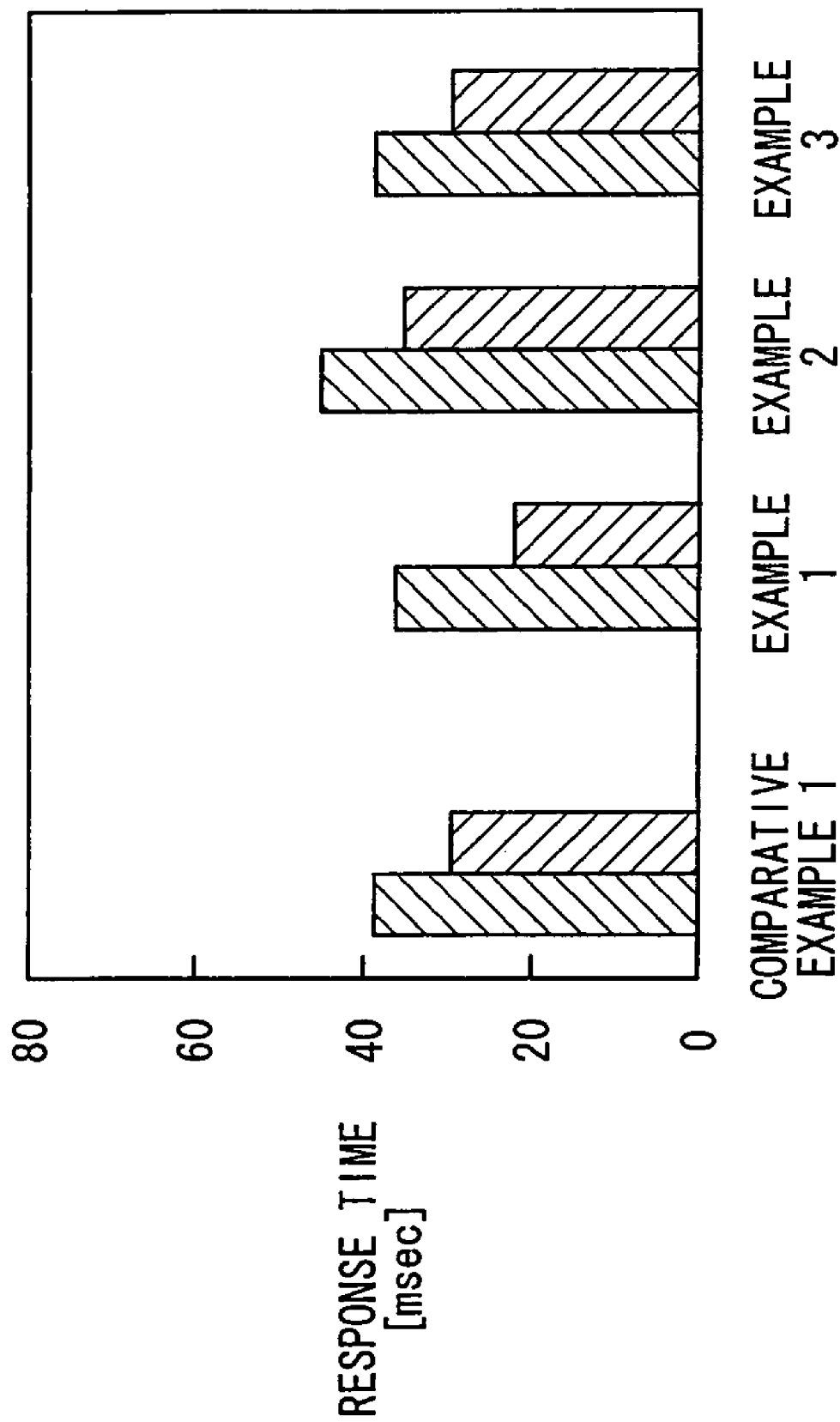
FIG. 13 shows a graph illustrating results of measurement of the response time with respect to the change of A/F.
Figure 14:
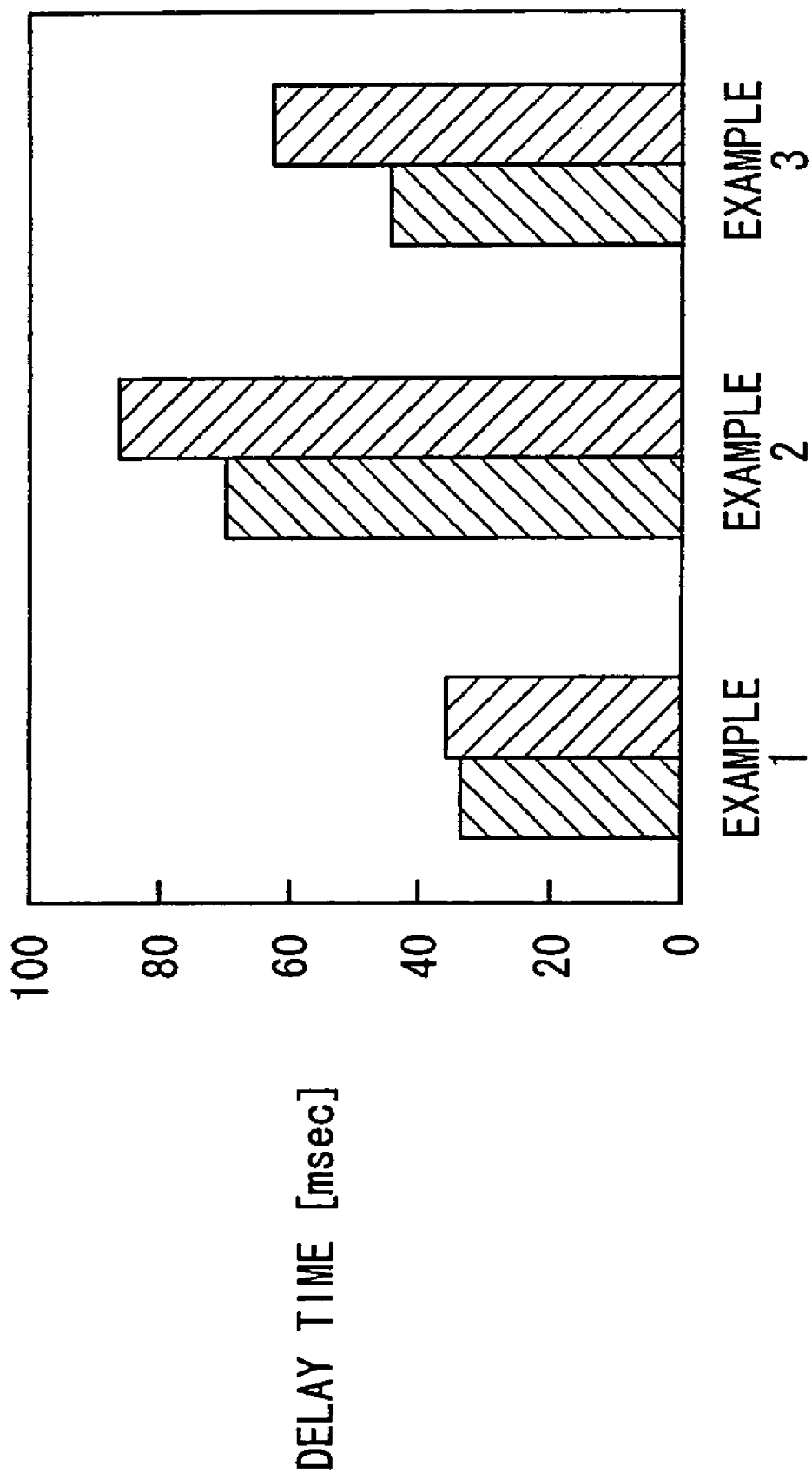
FIG. 14 shows a graph illustrating results of measurement of the delay time with respect to the change of A/F.

FIG. 13 shows results of the measurement of the response times T1, T2 in Comparative Example 1 and Examples 1 to 3, and FIG. 14 shows the delay times T3, T4 in Examples 1 to 3.

According to FIGS. 13 and 14, the following fact is appreciated. Example 1 involves the delay of a degree of about 30 msec as compared with Comparative Example 1, but the response time T1 in Example 1 is shorter than that in Comparative Example 1. Example 2 involves the delay of a degree of about 70 to 80 msec as compared with Comparative Example 1, and the response time T1 in Example 2 is longer than that in Comparative Example 1 by about 10 msec. Example 3 involves the delay of a degree of about 40 msec to 60 msec as compared with Comparative Example 1, but the response time T1 is scarcely changed between Comparative Example 1 and Example 3.

Next, in the third exemplary experiment, an observation was made for the response performance obtained when the NOx concentration in a combustion gas of propane was changed for Comparative Example 1 and Examples 1 to 3 described above. The gas temperature was 380° C., and the flow rate was 10 m/s.

Figure 15:
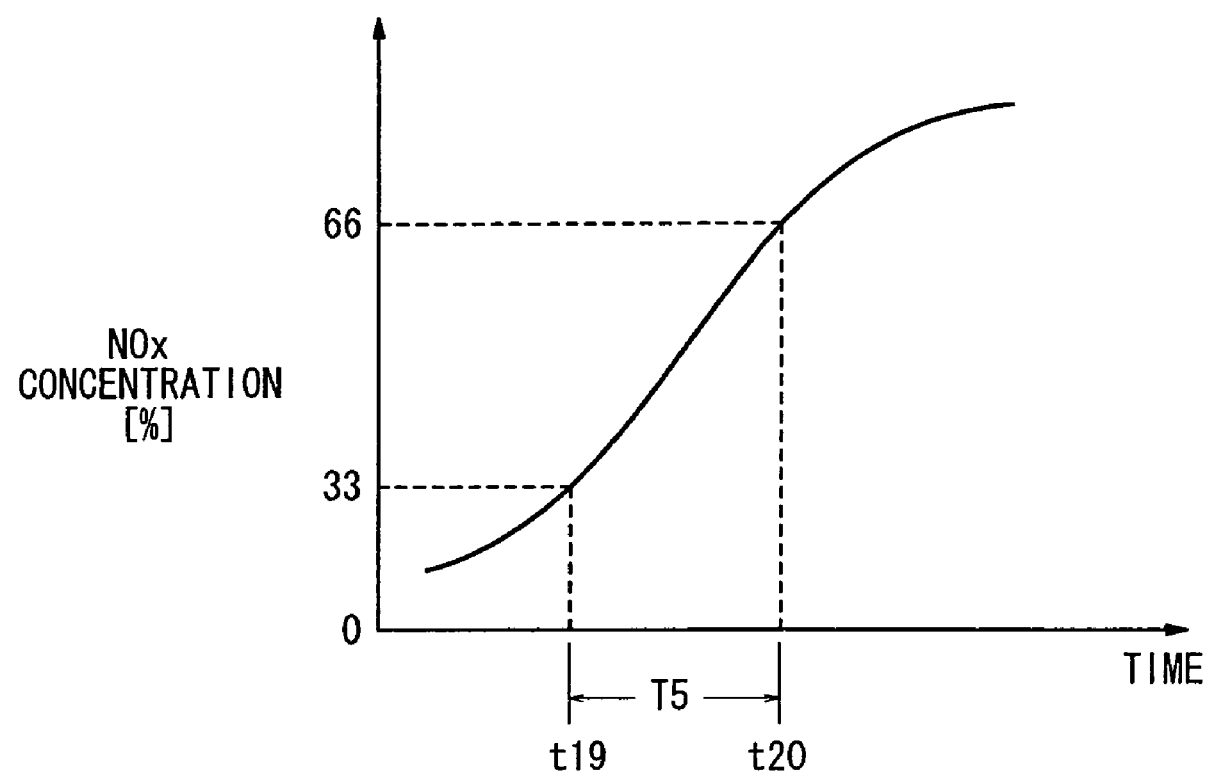
FIG. 15 illustrates the response time obtained when the NOx concentration is changed from 33% to 66%.
Figure 16:
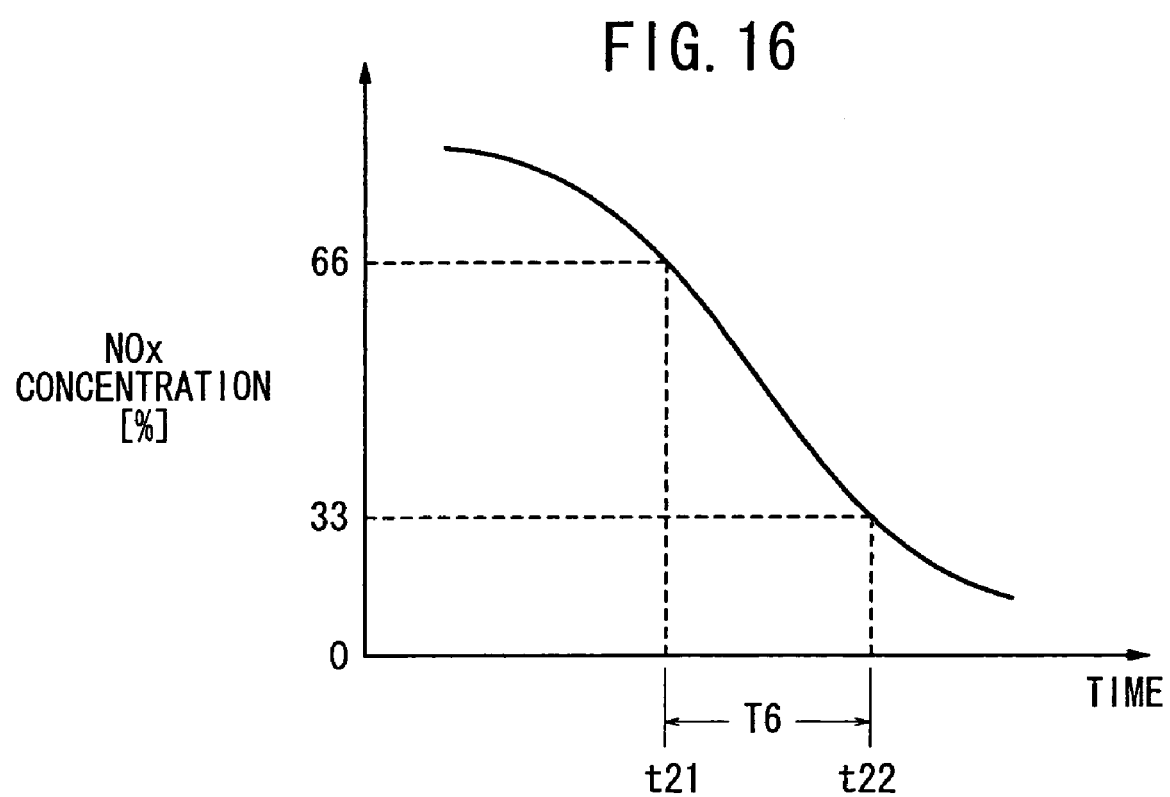
FIG. 16 illustrates the response time obtained when the NOx concentration is changed from 66% to 33%.

As shown in FIG. 4, the gas sensor 10 was attached perpendicularly to the exhaust tube 54. As shown in FIG. 15, a response time T5 was measured. The response time T5 ranged from a time point t19 at which the gas sensor 10 detected the NOx concentration=33% to a time point t20 at which the gas sensor 10 detected the NOx concentration=66% when the NOx concentration in the gas was changed from low concentration to high concentration. Further, as shown in FIG. 16, a response time T6 was measured. The response time T6 ranged from a time point t21 at which the gas sensor 10 detected the NOx concentration=66% to a time point t22 at which the gas sensor 10 detected the NOx concentration=33% when the NOx concentration in the gas was changed from high concentration to low concentration.

Figure 17:
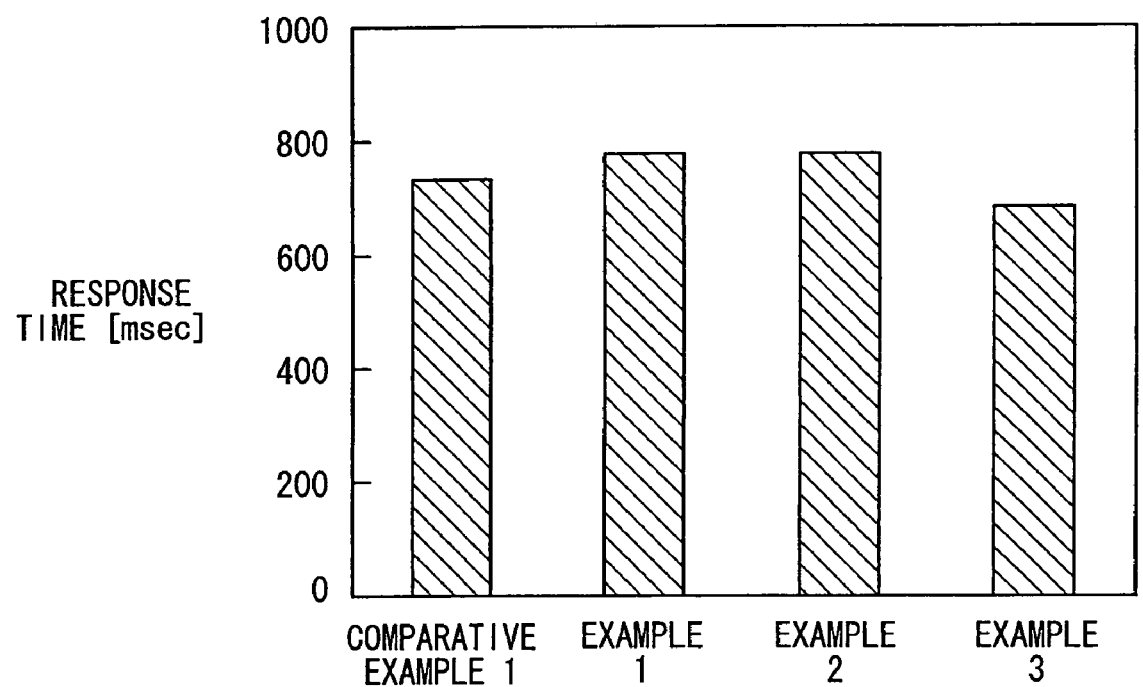
FIG. 17 shows a graph illustrating results of measurement of the response time with respect to the change of the NOx concentration.

FIG. 17 shows results of the measurement of the response times T5, T6 for Comparative Example 1 and Examples 1 to 3. Both of the response times T5, T6 of Comparative Example 1 were about 750 msec. Both of the response times T5, T6 of Example 1 were about 790 msec. Both of the response times T5, T6 of Example 2 were about 800 msec. Both of the response times T5, T6 of Example 3 were about 700 msec.

As described above, it is appreciated that Comparative Example 1 and Examples 1 to 3 had the approximately identical response times.

As described above, in Examples 1 to 3, the ratio A1/A2 between the total opening area A1 of the inner gas inlet holes 22 and the total opening area A2 of the outer gas inlet holes 34 is not less than 1. Therefore, the flow rate of the measurement gas to flow into the inner gas inlet holes 22 may be low, and the response performance of the sensor element 12 may be deteriorated. However, as appreciated from the second exemplary experiment and the third exemplary experiment, it is possible to suppress the deterioration of the response performance by appropriately selecting the diameters of the outer gas inlet holes 34 and the diameters of the inner gas inlet holes 22.

Figure 18:
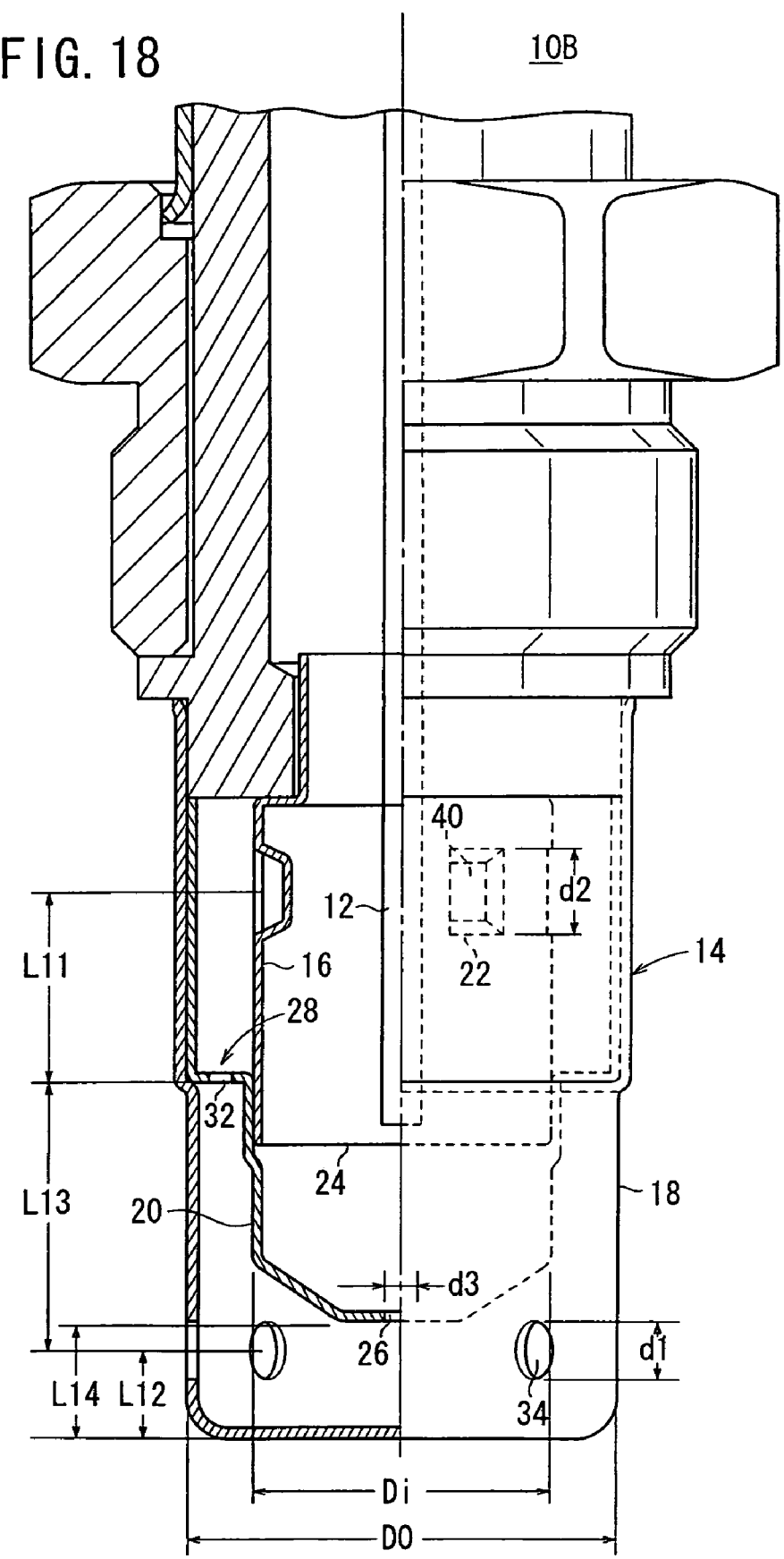
FIG. 18 is a sectional view illustrating, with partial omission, a gas sensor according to a second embodiment.

Next, a gas sensor 10B according to a second embodiment will be explained with reference to FIG. 18.

The gas sensor 10B according to the second embodiment is configured in approximately the same manner as the gas sensor 10A according to the first embodiment described above. However, as shown in FIG. 18, the gas sensor 10B is different from the gas sensor 10A in that plate sections 40 are provided for the inner protective cover 16 to extend over rectangular inner gas inlet holes 22, and the number of the inner gas inlet holes 22 is six.

Further, the gas sensor 10B is also different from the gas sensor 10A in that the flange section 28 of the intermediate protective cover 20 is positioned lower than that in the first embodiment, and the positional relationship of the outer gas inlet holes 34, the slits 32, and the inner gas inlet holes 22 is established such that the outer gas inlet holes 34, the slits 32, and the inner gas inlet holes 22 are arranged in this order from the bottom to an upper part of the outer protective cover 18.

Figure 19:
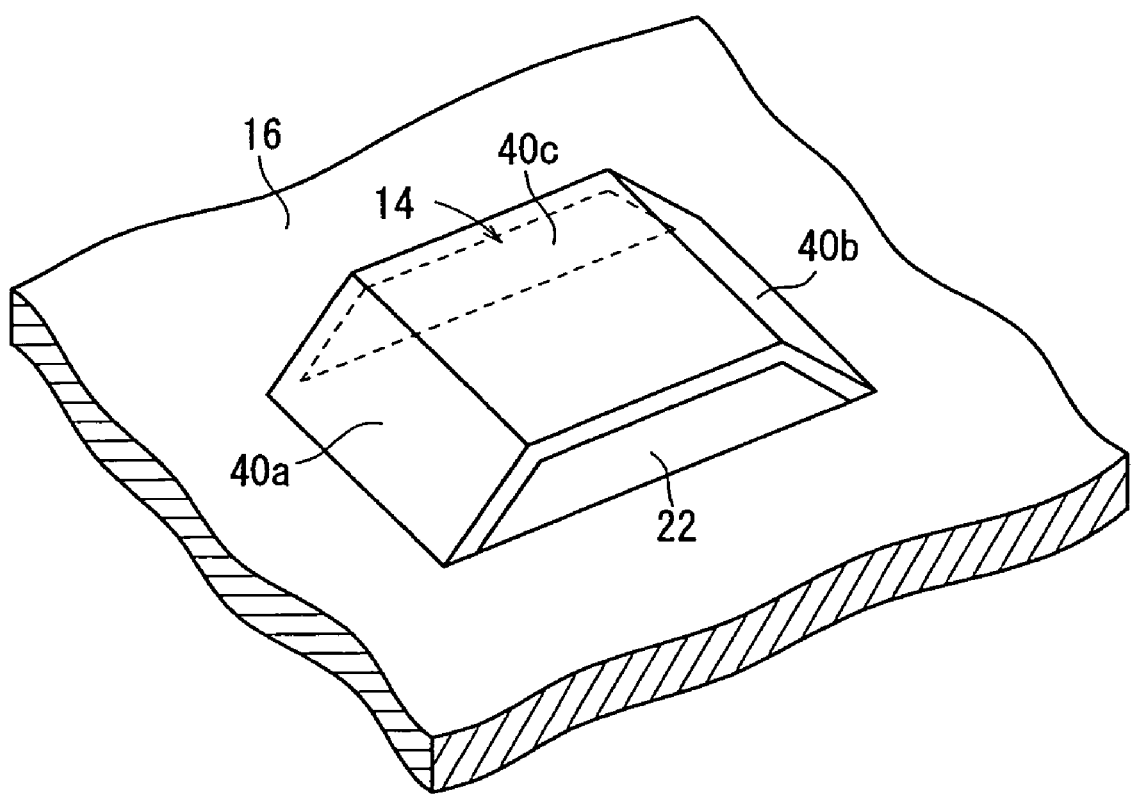
FIG. 19 is a perspective view illustrating a plate section extending over an inner gas-inlet hole.

As shown in FIG. 19, each of the plate sections 40 includes two side walls 40a, 40b which rise toward the center of the inner protective cover 16 from opposing circumferential portions of the inner gas inlet hole 22, and a flat plate section 40c which connects the side walls 40a, 40b integrally and which is in parallel to the opening of the inner gas inlet hole 22. In other words, the measurement gas passes through the portions other than the two side walls 40a, 40b and the flat plate section 40c.

Therefore, the flat plate section 40c gets the flow of the measurement gas coming into the inner gas inlet hole 22, and the measurement gas is diffused. The measurement gas flows through the inner gas inlet hole 22, and the measurement gas is transmitted to the sensor element 12 disposed in the inner protective cover 16. As described above, the sensor element 12 is prevented from any blow of the measurement gas, and it is possible to suppress the temperature change in the sensor element 12.

Specific dimensions of the protective cover 14 of the gas sensor 10B according to the second embodiment may be described as follows by way of example. That is, as for the outer protective cover 18, the outer diameter Do of the outer protective cover 18 is about 14.6 mm, the diameter d1 of the outer gas inlet hole 34 is about 2 mm, and the thickness of the outer protective cover 18 is about 0.4 mm.

As for the inner protective cover 16, the outer diameter Di is about 10 mm, the long side d2 of the inner gas inlet holes 22 is about 3 mm, and the thickness of the inner protective cover 16 is about 0.3 mm. The diameter d3 of the intermediate gas discharge hole 26 provided at the bottom of the intermediate protective cover 20 is about 1 mm.

The distance L11, which ranges from the flange section 28 to the center of the inner gas inlet hole 22, is about 6.3 mm. The distance L12, which ranges from the end of the outer protective cover 18 to the center of the outer gas inlet hole 34, is about 3 mm. The distance L13, which ranges from the center of the outer gas inlet holes 34 to the flange section 28, is about 7.5 mm. The distance L14, which ranges from the end of the outer protective cover 18 to the end of the intermediate protective cover 20, is about 4 mm.

It is a matter of course that the gas sensor according to the present invention is not limited to the embodiments described above, which may be embodied in other various forms without deviating from the gist or essential characteristics of the present invention.

As described above, according to the gas sensor concerning the present invention, it is possible to effectively reduce the droplets of water and the temperature change of the sensor element which would be otherwise caused by the inflow of the measurement gas, without deteriorating the response performance, and the temperature characteristics and the water resistance are excellent.

What is claimed is:

1. A gas sensor comprising a sensor element which measures a predetermined gas component of an introduced measurement gas, and a protective cover which surrounds said sensor element, said protective cover including:
   an inner protective cover which covers at least an end portion of said sensor element, an outer protective cover which covers said inner protective cover, and an intermediate protective cover which is installed between said inner protective cover and said outer protective cover, wherein
   said inner protective cover has a bottom-equipped cylindrical shape with a plurality of inner gas inlet holes which are formed at positions on a side surface thereof facing said sensor element and with at least one inner gas discharge hole which is formed at a bottom portion thereof;
   said outer protective cover has a bottom-equipped cylindrical shape with a plurality of outer gas inlet holes, said outer gas inlet holes being formed in a side surface of said outer protective cover at portions where said outer gas inlet holes do not face said inner gas inlet holes;
   said intermediate protective cover has at least intermediate gas inlet holes which are formed at positions where said intermediate gas inlet holes do not face said inner gas inlet holes and said outer gas inlet holes;
   A1/A2>1, provided that A1 represents a total opening area of said inner gas inlet holes, and A2 represents a total opening area of said outer gas inlet holes;
   the number of said inner gas inlet holes is greater than the number of said outer gas inlet holes and the area of each of said inner gas inlet holes is less than the area of each of said outer gas inlet holes; and
   the distance from the outer gas inlet holes to the intermediate gas inlet holes is greater than the distance from the intermediate gas inlet holes to the inner gas inlet holes.

2. The gas sensor according to claim 1, wherein said inner protective cover has plate sections each of which extends over each of said inner gas inlet holes.

3. The gas sensor according to claim 1, wherein said inner gas inlet holes are formed at approximately equal pitches along one circumference of said inner protective cover.

4. The gas sensor according to claim 1, wherein said inner gas inlet holes are classified into first, second, . . . and nth groups;
   inner gas inlet holes in said first group are formed at approximately equal pitches along a first circumference of said inner protective cover;
   inner gas inlet holes in said second group are formed at approximately equal pitches along a second circumference of said inner protective cover; and
   inner gas inlet holes in said nth group are formed at approximately equal pitches along an nth circumference of said inner protective cover.

5. The gas sensor according to claim 1, wherein said protective cover is attached substantially perpendicularly to a gas tube.

6. The gas sensor according to claim 1, wherein said protective cover is attached while being inclined to a gas tube.

* * * * *